United States Patent [19]
Lavielle et al.

[11] Patent Number: 5,348,968
[45] Date of Patent: Sep. 20, 1994

[54] INDOLE, INDAZOLE AND BENZISOXAZOLE COMPOUNDS

[75] Inventors: Gilbert Lavielle, La Celle Saint Cloud; Philippe Maillos, Villejuif; Olivier Muller, Ennery; Michel Laubie, Vaucresson; Tony Verbeuren, Vernouillet; Jean-Jacques Descombes, Neuilly-Plaisance, all of France

[73] Assignee: Adir et Compagnie, Courbevoie, France

[21] Appl. No.: 189,798

[22] Filed: Feb. 1, 1994

[30] Foreign Application Priority Data
Feb. 2, 1993 [FR] France .................... 93 01054

[51] Int. Cl.⁵ .................. A61K 31/41; A61K 31/415; C07D 209/08; C07D 231/56
[52] U.S. Cl. .................... 514/360; 514/362; 514/364; 514/379; 514/403; 514/414; 548/125; 548/131; 548/134; 548/241; 548/361.1; 548/362.5; 548/468; 548/311.7; 548/312.1
[58] Field of Search ........... 548/131, 125, 134, 361.1, 548/362.5, 241, 468, 311.7, 312.1; 514/364, 360, 362, 403, 379, 414, 397

[56] References Cited
PUBLICATIONS
CA 87(11): 84761f Derivatives of Indole . . . Sulfomethylate, Valezheva et al., p. 574, 1977.
CA 113(9): 77713u Catalytic Palladium–Mediated . . . Reagents, Takacs et al, p. 722, 1990.

*Primary Examiner*—Robert W. Ramsuer
*Assistant Examiner*—Joseph K. McKane
*Attorney, Agent, or Firm*—Gordon W. Hueschen

[57] ABSTRACT

The invention relates to a compound of formula (I):

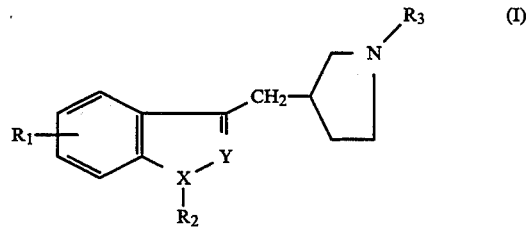

in which:
$R_1$ represents hydrogen or halogen, alkyl, alkoxy, cyano or aminocarbonyl or any one of the following:

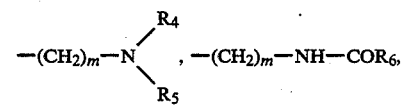

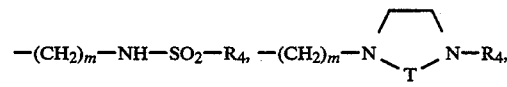

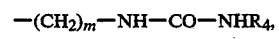

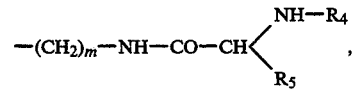

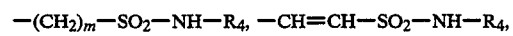

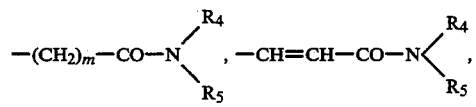

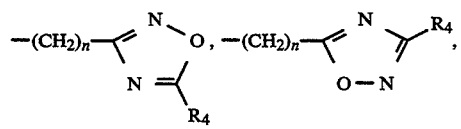

(Abstract continued on next page.)

-continued

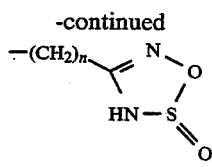

in which:
- m is equal to 1, 2 or 3,
- n is equal to 0, 1 or 2,
- T represents a CO or SO$_2$,
- R$_4$ or R$_5$, which are identical or different, represent hydrogen or alkyl or phenyl,
- R$_2$ represents hydrogen or alkyl, phenyl or acyl,
- R$_3$ represents hydrogen, alkyl (optionally substituted by hydroxyl or phenyl) or alkoxycarbonyl,
- —X—Y= represents —N—C=, —N—N=or else

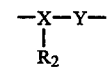

represents —O—N=;

to its enantiomers, diastereoisomers and epimers and to its addition salts with a pharmaceutically acceptable acid.

11 Claims, No Drawings

INDOLE, INDAZOLE AND BENZISOXAZOLE COMPOUNDS

The present invention relates to new indole, indazole and benzisoxazole compounds. Many indole derivatives have been described in the literature. Some of them have been developed as agonists of 5-HT$_1$-like receptors for the treatment and prevention of pain caused by abnormal vascular flow such as migraine and associated illnesses. This is the case more particularly of the compounds described in Patents EP 382,570, DE 3,131,728, EP 438,230 and EP 486,666.

Patent EP 135,781 describes, for its part, indazole derivatives as central analgesics having neuro-leptic properties.

The compounds of the present invention, apart from the fact that they are new, have particularly intense pharmacological properties.

More specifically, the present invention relates to compounds of formula (I):

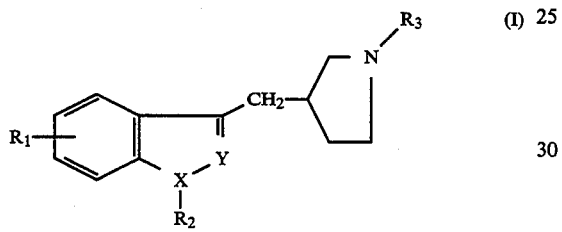

in which:

R$_1$ represents a hydrogen or halogen atom, a linear or branched (C$_1$-C$_6$)alkyl, linear or branched (C$_1$-C$_6$)alkoxy, cyano or aminocarbonyl group or any one of the following groups:

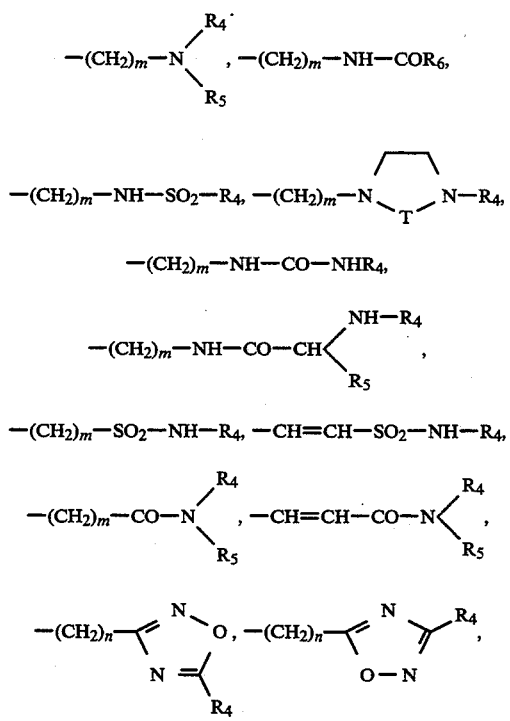

-continued

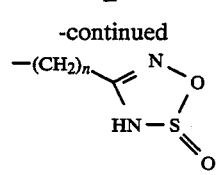

in which:
m is equal to 1, 2 or 3,
n is equal to 0, 1 or 2,
T represents a CO or SO$_2$,
R$_4$ or R$_5$, which are identical or different, represent a hydrogen atom, a linear or branched (C$_1$-C$_6$)alkyl group or a phenyl group (unsubstituted or substituted by one or a number of halogen atoms or alkyl, alkoxy or trihalomethyl groups),
R$_2$ represents a hydrogen atom, a linear or branched (C$_1$-C$_6$)alkyl group, a phenyl group (unsubstituted or substituted by one or a number of halogen atoms or alkyl, alkoxy or trihalomethyl groups) or an acyl group,
R$_3$ represents a hydrogen atom, a linear or branched (C$_1$-C$_6$)alkyl group (optionally substituted by a hydroxyl group or a phenyl group (itself unsubstituted or substituted by one or a number of halogen atoms or alkyl, alkoxy or trihalomethyl groups)) or a linear or branched (C$_1$-C$_6$)alkoxycarbonyl group,
—X—Y= represents —N—C=, —N—N= or else

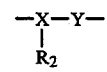

represents —O—N=;
to their enantiomers, diastereoisomers and epimers and to their addition salts with a pharmaceutically acceptable acid.

Among pharmaceutically acceptable acids, mention may be made, as non-limiting, of hydrochloric, hydrobromic, sulfuric, phosphonic, acetic, trifluoroacetic, lactic, pyruvic, malonic, succinic, glutaric, fumaric, tartaric, maleic, citric, ascorbic, methanesulfonic, camphoric and oxalic acids and the like.

The present invention also relates to the process for the synthesis of the compounds of formula (I).

The process for the preparation of the compounds of formula (I), for which

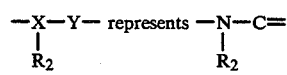

is distinguished in that an isatin of formula (II) obtained according to the processes described by V. Q. Yen et al. (J. Org. Chem., 23, 1858, 1958) and C.S. Marvel et al. (Org. Synth. Coll., Vol. I, 327):

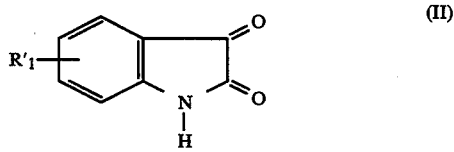

in which R'$_1$ represents a hydrogen or halogen atom or a linear or branched (C$_1$-C$_6$)alkyl or linear or branched ($C_1$-$C_6$)alkoxy group, is used as starting material, is converted to the corresponding sodium anion in the presence of sodium hydride, and is then condensed with the magnesium compound of formula (III):

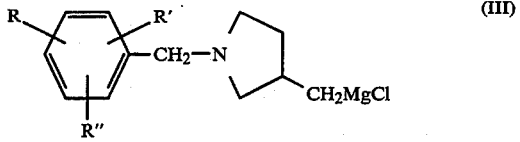
(III)

in which R, R' and R'', which are identical or different, represent a halogen atom or an alkyl, alkoxy or trihalomethyl group, to lead to the compound of formula (IV):

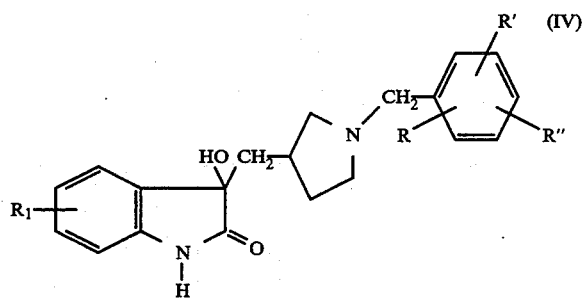
(IV)

in which R'$_1$, R, R' and R'' have the same meaning as above, which is subjected to the action of lithium aluminum hydride to lead to the compound of formula (I/a):

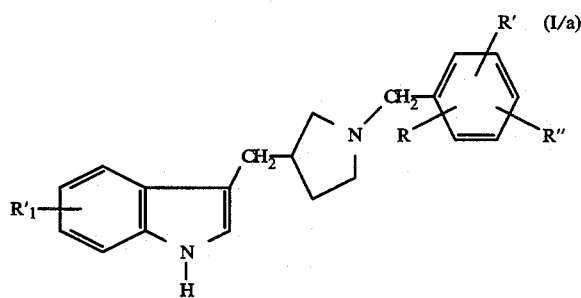
(I/a)

in which R'$_1$, R, R' and R'' have the same meaning as above, compound of formula (I/a) in which the R'$_1$ radical, when it represents a bromine atom, is converted, if desired, to the cyano group and then to one of the other groups as defined in the formula (I), according to standard organic chemistry techniques, and which is optionally subjected to, the action of hydrochloric acid in ethanolic solution followed by debenzylation by hydrogenolysis to lead to the compound of formula (I/b), a specific case of the compounds of formula (I):

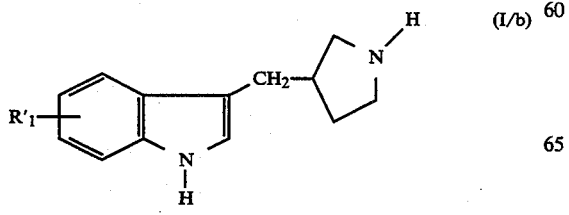
(I/b)

in which R$_1$ has the same meaning as in the formula (I), and then, if desired, the action of the halogenated derivative of formula (V):

BrB'$_3$ (V)

in which R'$_3$ represents a linear or branched ($C_1$-$C_6$)-alkyl group optionally substituted by a hydroxyl group, to lead to the compound of formula (I/c), a specific case of the compounds of formula (I):

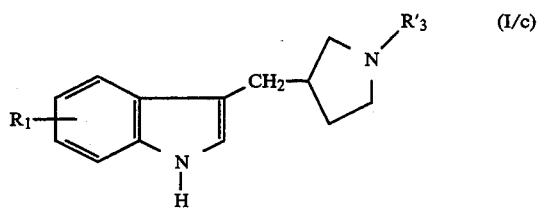
(I/c)

in which R$_1$ and R'$_3$ have the same meaning as above, which compound of formula (I/a), (I/b) or (I/c) is subjected, if appropriate, to the action of a substituted or unsubstituted iodinated benzene compound, in the presence of copper, of an alkyl halide or of an acyl halide, to lead to the compound of formula (I/d), a specific case of the compounds of formula (I):

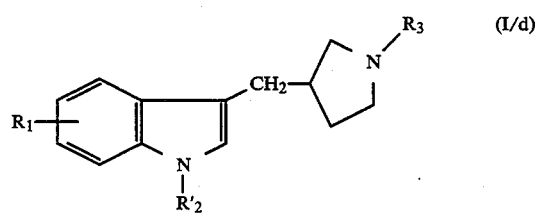
(I/d)

in which R$_1$ and R$_3$ have the same meaning as in the formula (I) and R'$_2$ represents a linear or branched ($C_1$-$C_6$)alkyl group, a phenyl group (unsubstituted or substituted by one or a number of halogen atoms or alkyl, alkoxy or trihalomethyl groups) or an acyl group, which compound of formula (I/a), (I/b), (I/c) or (I/d), is purified, if appropriate, according to a standard purification technique, is separated, if desired, into the isomers according to a standard purification technique, and is optionally converted to its addition salts with a pharmaceutically acceptable acid.

The process for the preparation of the compounds of formula (I) for which

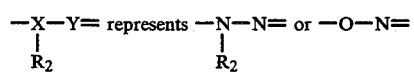

is distinguished in that a magnesium compound of formula (III):

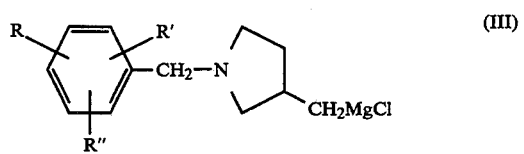
(III)

in which R, R' and R'', which are identical or different, represent a halogen atom or an alkyl, alkoxy or trihalomethyl group, is condensed with an aromatic nitrile of formula (VI):

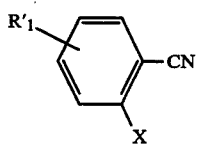

in which R'₁ represents a hydrogen or halogen atom or a linear or branched (C₁–C₆)alkyl or linear or branched (C₁–C₆)alkoxy group and X represents a halogen atom, to lead to the compound of formula (VII):

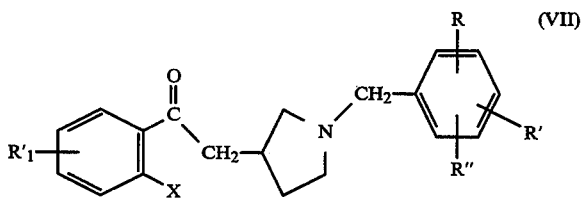

in which R'₁, X, R, R' and R" have the same meaning as above, which is reacted, depending on the nature of the compound of formula (I) which it is desired to obtain,
  either with hydrazine in dimethyl sulfoxide,
  or with hydroxylamine according to the process described in Patent EP 196,132, to lead to the compound of formula (I/e), a specific case of the compounds of formula (I):

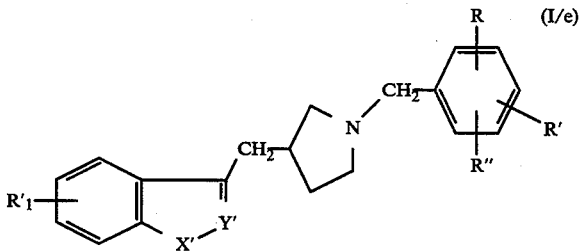

in which R'₁, R, R' and R" have the same meaning as above, and —X'—Y'= represents

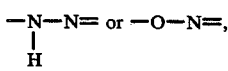

compound of formula (I/e) in which the R'₁ radical, when it represents a halogen atom, is converted, if desired, to the cyano group and then to one of the other groups as defined in the formula (I), according to standard organic chemistry techniques, and which is optionally subjected:
  either to the action of hydrochloric acid in ethanolic solution and debenzylated by hydrogenolysis, to lead to the compound of formula (I/f), a specific case of the compounds of formula (I):

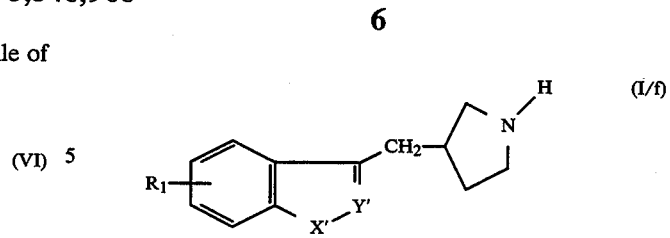

in which R₁ and —X'—Y'= have the same meaning as above,
  or to the action of the halogenated derivative of formula (V):

$$BrB'_3 \quad (V)$$

in which R'₃ represents a linear or branched (C₁–C₆)-alkyl group optionally substituted by a hydroxyl group, to lead to the compound of formula (I/g), a specific case of the compounds of formula (I):

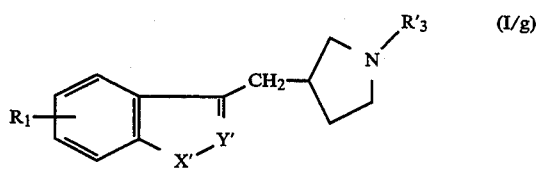

in which R₁, R'₃ and —X'—Y'= have the same meaning as above, which compound of formula (I/e), (I/f) or (I/g), when:
—X'—Y'=represents

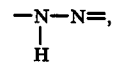

can be subjected to the action of a substituted or unsubstituted iodinated derivative of benzene, in the presence of copper, or of an alkyl halide or of an acyl halide, to lead to the compound of formula (I/h), a specific case of the compounds of formula (I):

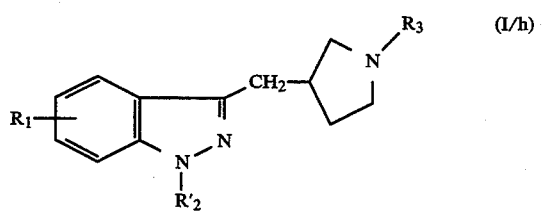

in which R₁ and R₃ have the same meaning as in the formula (I) and R'₂ represents a linear or branched (C₁–C₆)alkyl group, a phenyl group (unsubstituted or substituted by one or a number of halogen atoms or alkyl, alkoxy or trihalomethyl groups) or an acyl group, which compound of formula (I/e), (I/f), (I/g) or (I/h),
  is purified, if appropriate, according to a standard purification technique,
  is separated, if desired, into the isomers according to a standard purification technique,
  and is optionally converted to its addition salts with a pharmaceutically acceptable acid.

The compounds of formula (I) such that R₁ represents a group:

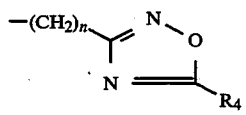

can be prepared from a compound of formula (I₁), a specific case of the compounds of formula (I):

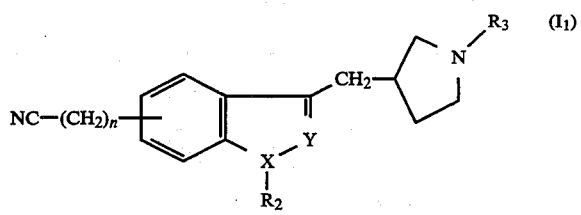

in which X, Y, n, $R_2$ and $R_3$ have the same meaning as in the formula (I), which is reacted, in a first step, with hydroxylamine and then, in a second step, with an acid anhydride or an ester to lead to the compound of formula (I₂), a specific case of the compounds of formula (I):

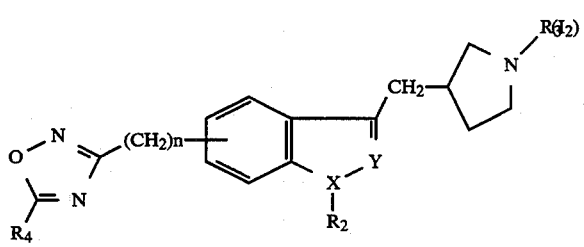

in which X, Y, $R_2$, $R_3$, $R_4$ and n are as defined in the formula (I).

The compounds of formula (I) such that $R_1$ represents a group:

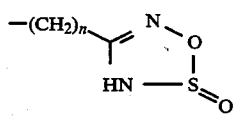

can be prepared from a compound of formula (I₁) as defined above, which is reacted, in a first step, with hydroxylamine and then, in a second step, with thionyl chloride to lead to the compound of formula (I₃), a specific case of the compounds of formula (I):

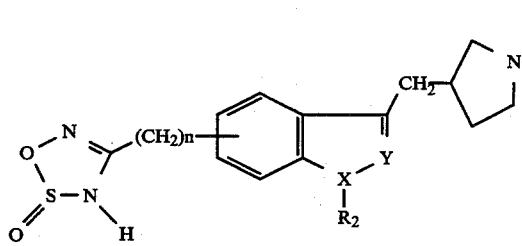

in which $R_2$, $R_3$, X, Y and n have the same meaning as above.

The compounds of formula (I) such that $R_1$ represents a group:

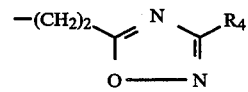

can be prepared from a compound of formula (I₁) as defined above in which the nitrile group is converted to an acid, and then an ester, group, which is then subjected to the action of the oxime $R_4C(NH_2)=NOH$ in the presence of sodium hydride to lead to the compound of formula (I₄), a specific case of the compounds of formula (I):

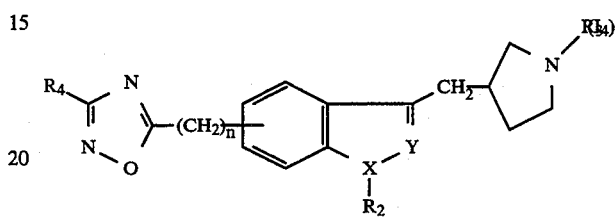

in which $R_2$, $R_3$, $R_4$, n, X and Y have the same meaning as in the formula (I).

The compounds of the present invention are powerful agonists at 5-HT₁-like receptors and can be used in the treatment of depression, anxiety, migraine, pain and illnesses associated with a deficiency of serotoninergic neurotransmission as has been shown by P. P. A. Humphrey et al. (5-Hydroxytryptamine Mechanisms in Primary Headaches, p. 213–219, edited by J. Olesen and P. R. Saxena, Raven Press, N.Y., 1992).

The compounds of the invention have been evaluated as antimigraine agents in comparison with a reference compound, sumatriptan, in a pharmacological test measuring the contraction of the vena saphena isolated from dogs or rabbits as described by P. Humphrey et al. (Br. J. Pharmacol., 94, 1128, 1988).

The invention also applies to the pharmaceutical compositions containing, as active principle, at least one compound of formula (I) with one or a number of inert, nontoxic and suitable excipients. The pharmaceutical compositions thus obtained can be provided in various forms, the most advantageous being tablets, sugar-coated tablets, gelatin capsules, suppositories, drinkable suspensions, and the like.

The useful dose can be varied depending on the nature and the severity of the ailment, the administration route and depending on the age and the weight of the patient. This unit dose varies from 0.1 to 100 mg per day taken once or a number of times.

The following examples illustrate the invention but do not limit it in any way. The starting materials used are starting materials which are known or prepared according to known procedures.

EXAMPLE 1

3-[(1-Benzylpyrrolidin-3-yl)methyl]-5-fluoroindole

Stage A:
3-Hydroxy-3-[(1-benzylpyrrolidin-3-yl)methyl]-5-fluoro-2-oxoindole

A solution of a magnesium compound is prepared, on the one hand, from 334 mmol of 1-benzyl-3-chloromethylpyrrolidine, 334 mmol of magnesium and 300 ml of tetrahydrofuran (THF). On the other hand, a solution containing [lacuna] is prepared from 303 mmol of 5-fluoroisatin and 303 mmol of sodium hydride in 500 ml of THF. The solution containing the magnesium compound is added at 0° C. to the second solution containing the sodium anion of the isatin. The combined mixture is left for 3 hours at room temperature and then brought to reflux for 12 hours. The reaction mixture is then hydrolyzed while cold with 1 kg of ice and 500 ml of water containing 60 ml of glacial acetic acid. The expected product is then extracted with dichloromethane and obtained in the form of an oil, after drying, evaporation and purification by chromatography on a silica column, using a dichloromethane/methanol/aqueous ammonia (98/2/0.2) mixture as eluent.

Yield: 65%
Infrared spectrum (nujol):
$\nu_{OH/NH}$: between 3500 and 2400 cm$^{-1}$
$\nu_{CO}$: 1712 cm$^{-1}$ Stage B:
3-[(1-Benzylpyrrolidin-3-yl)methyl]-5-fluoroindole A solution containing 33.7 mmol of the product obtained in the preceding stage in 300 ml of THF at 20° C. is added to a suspension containing 33.7 mmol of lithium aluminum hydride in 200 ml of THF. After 2 hours at room temperature, the combined mixture is brought to reflux for 2 hours and is then hydrolyzed with 20 ml of water, 28.5 ml of 10% sodium hydroxide solution and 55 ml of water. After extracting with dichloromethane, drying and evaporation, the expected product is obtained in the form of an oil after purification by chromatography on a silica column, using a dichloromethane/methanol/aqueous ammonia (98/2/0.2) mixture as eluent.

Yield: 75%
Infrared spectrum (nujol):
$\nu_{NH}$: 3263 cm$^{-1}$

EXAMPLE 2

3-[(Pyrrolidin-3-yl)methyl]-5-fluoroindole, oxalate 24.5 mmol of the compound obtained in Example 1 in 150 ml of ethanol and one equivalent of gaseous hydrochloric acid are debenzylated, under a hydrogen atmosphere, at 20° C., using 0.8 g of palladium as catalyst. After filtering the solution and concentrating, the expected product is converted to a salt with one equivalent of oxalic acid in ethanol.

Yield: 95%
Melting point: 180° C.

| Elemental microanalysis: | | | |
|---|---|---|---|
| | C % | H % | N % |
| calculated | 58.44 | 5.56 | 9.09 |
| found | 59.15 | 5.68 | 8.91 |

EXAMPLE 3

3-[(1-Propylpyrrolidin-3-yl)methyl]-5-fluoroindole oxalate 9 mmol of the product obtained in Example 2, 9 mmol of 1-bromopropane and 20 mmol of sodium carbonate are brought to 60° C. for 8 hours in 50 ml of acetonitrile.

After evaporation, taking up in water, extraction with dichloromethane, drying and evaporation, the expected product is obtained in the form of an oil and is purified by chromatography on a silica column, using a dichloromethane/methanol/aqueous ammonia (96/4/0.4) mixture as eluent. It is converted to the oxalate in oxalic ether.

Melting point: 80° C.

| Elemental microanalysis: | | | |
|---|---|---|---|
| | C % | H % | N % |
| calculated | 61.70 | 6.62 | 7.99 |
| found | 61.95 | 6.55 | 7.85 |

EXAMPLE 4

3-[(1-Benzylpyrrolidin-3-yl)methyl]-5-methoxyindole, hydrochloride

This compound was synthesized according to the same procedure as that described for Example 1 and was converted to the corresponding hydrochloride.

Melting point: 115° C.

| Elemental microanalysis: | | | |
|---|---|---|---|
| | C % | H % | N % | Cl % |
| calculated | 70.67 | 7.06 | 7.85 | 9.93 |
| found | 70.55 | 7.06 | 7.68 | 10.31 |

EXAMPLE 5

3-[(Pyrrolidin-3-yl)methyl]-5-methoxyindole, hydrochloride

This compound was synthesized according to the process described for Example 2 using the compound of Example 4.

The proton nuclear magnetic resonance spectrum shows the disappearance of the signals corresponding to the benzyl group.

EXAMPLE 6

3-[(1-Benzylpyrrolidin-3-yl)methyl]-5-methylindole, hydrochloride

This compound was synthesized according to the same procedure as that described by Example 1 and was converted to the corresponding hydrochloride.

Yield: 90%
Missing point: 95° C.

| Elemental microanalysis: | | | |
|---|---|---|---|
| | C % | H % | N % | Cl % |
| calculated | 73.99 | 7.39 | 8.22 | 10.40 |
| found | 73.73 | 7.33 | 8.19 | 10.16 |

EXAMPLE 7

3-[(Pyrrolidin-3-yl)methyl]-5-methylindole

This compound was synthesized according to the same process as that described for Example 2 using the compound of Example 6.

Yield: 80%

The proton nuclear magnetic resonance spectrum shows the disappearance of the signals corresponding to the benzyl group.

EXAMPLE 8

3-[(1-Propylpyrrolidin-3-yl)methyl]-5-methylindole, hydrochloride

This compound was synthesized according to the same process as that described in Example 3 using the compound of Example 7.

Yield: 54%

| Elemental microanalysis: | C % | H % | N % | Cl % |
|---|---|---|---|---|
| calculated | 69.72 | 8.60 | 9.57 | 12.11 |
| found | 70.23 | 8.64 | 9.14 | 11.85 |

EXAMPLE 9

3-[(1-Benzylpyrrolidin-3-yl)methyl-5-chloroindole

This compound was synthesized according to the same process as that described for Example 1.

Yield: 85%

Infrared spectrum (nujol):

$v_{NH}$: 3265 cm$^{-1}$

EXAMPLE 10

3-[(Pyrrolidin-3-yl)methyl]-5-chloroindole

This compound was synthesized according to the same process as that described for Example 2 using the compound of Example 9.

The proton nuclear magnetic resonance spectrum shows the disappearance of the signals corresponding to the benzyl group.

EXAMPLE 11

1-(4-Fluorophenyl)-3-[(1-benzylpyrrolidin-3-yl)methyl-5-chloroindole, oxalate 11 mmol of the compound of Example 9, 16 mmol of 1-fluoro-4-iodobenzene, 16 mmol of potassium carbonate, 1.5 mmol of copper bronze and 6.6 mmol of copper bromide are brought to 180° C. in 25 ml of N-methylpyrrolidone for 6 hours. The combined mixture is hydrolyzed with 150 ml of 1N hydrochloric acid and 20 ml of isopropyl ether. The hydrochloride obtained is filtered, taken up in sodium hydroxide solution and extracted with dichloromethane. After drying and evaporation, the expected product is purified by chromatography on a silica column, using a dichloromethane/methanol (97/3) mixture as eluent. The oil obtained after concentration is then converted to a salt with one equivalent of oxalic acid in ethanol.

Yield: 70%

Melting point: 196° C.

| Elemental microanalysis: | C % | H % | N % | Cl % |
|---|---|---|---|---|
| calculated | 66.08 | 5.15 | 5.50 | 6.97 |
| found | 66.22 | 5.24 | 5.43 | 7.18 |

EXAMPLE 12

3-[(1-Benzylpyrrolidin-3-yl)methyl]-5-bromoindole, oxalate

This compound was synthesized by using the same process as that described in Example 1.

Yield: 60%

EXAMPLE 13

3-[(Pyrrolidin-3-yl)methyl]-5-bromoindole, oxalate

This compound was synthesized using the same process as that described for Example 2 using the compound of Example 12.

EXAMPLE 14

3-[(1-Benzylpyrrolidin-3-yl)methyl]-5-cyanoindole 13.5 mmol of the compound of Example 12 and 16 mmol of copper cyanide are brought to reflux in 50 ml of N-methylpyrrolidone for 150 minutes.

The combined mixture is hydrolyzed with 50 ml of ice and 30 ml of aqueous ammonia. After extracting the dichloromethane, drying and evaporation, the expected product is purified by chromatography on a silica column, using a dichloromethane/methanol/aqueous ammonia (96/4/0.4) mixture as eluent.

Yield: 55%

EXAMPLE 15

3-[(1-Benzylpyrrolidin-3-yl)methyl]-5-aminocarbonylindole 0.47 mmol of the compound obtained in Example 14 and 1 g of polyphosphoric acid are heated at 85° C. for 90 minutes. The combined mixture is then hydrolyzed with a water/ice mixture and the pH of this solution brought to 11-12 using concentrated sodium hydroxide solution. After extraction with a chloroform/methanol (80/15) mixture, drying and evaporation, the expected product is purified by chromatography on a silica column, using a THF/hexane/methanol/aqueous ammonia (80/18/2/0.2) mixture as solvent.

Yield: 60%

Infrared spectrum (nujol):

$v_{NH_2}$: 3182 cm$^{-1}$ $v_{CO}$(amide): 1651 cm$^{-1}$

EXAMPLE 16

3-[(Pyrrolidin-3-yl)methyl]-5-aminocarbonylindole

This compound is obtained according to the same process as that described for Example 2 using the compound of Example 15.

Yield: 86%

The proton nuclear magnetic resonance spectrum shows the disappearance of the signals corresponding to the benzyl group.

EXAMPLE 17

3-[(1-Propylpyrrolidin-3-yl)methyl]-5-aminocarbonylindole, oxalate

This compound is obtained using the same process as that described for Example 3 using the compound of Example 16.

Yield: 60%

| Elemental microanalysis: | C % | H % | N % |
|---|---|---|---|
| calculated | 60.79 | 6.71 | 11.19 |
| found | 60.92 | 6.53 | 10.83 |

EXAMPLE 18

3-[(1-Benzylpyrrolidin-3-yl)methyl]-6-fluoro-1H-indazole, oxalate

Stage A:
1-Benzyl-3-[(2,4-difluorobenzoyl)methyl]-pyrrolidine

A solution containing 238 mmol of 1-benzyl-3-chloromethylpyrrolidine in 400 ml of ether is added to a suspension containing 238 mmol of magnesium in 100 ml of ether. The combined mixture is brought to reflux until the metal has disappeared. After cooling, 238 mmol of 2,4-difluorobenzonitrile in 200 ml of ether are added to this solution. The mixture is brought to reflux for 24 hours, is then hydrolyzed with 78 ml of concentrated hydrochloric acid and 50 ml of water and again brought to boiling point for 2 hours. After cooling and separation by settling, the aqueous phase is brought to pH 10 and extracted with dichloromethane. The expected product is obtained in the form of an oil after drying, evaporation and purification by chromatography on a silica column, using a dichloromethane/methanol/aqueous ammonia (99/1/0.1) mixture as eluent.

Infrared spectrum (nujol)
$v_{CO}$: 1687 cm$^{-1}$

Stage B: 3-[(1-Benzylpyrrolidin-3-yl)methyl]-6-fluoro-1H-indazole, oxalate

16 mmol of the compound obtained in the preceding stage and 16 mmol of hydrazine in 50 ml of n-butanol are heated for 72 hours at reflux. After evaporating the solvent, the residue is taken up in 100 ml of water, extracted with dichloromethane, dried and evaporated. The expected product is purified by chromatography on a silica column, using the dichloromethane/methanol/aqueous ammonia (97/3/0.3) mixture as eluent and transformed in the corresponding oxalate.

Infrared spectrum (nujol):
$v_{NH}$: 3165 cm$^{-1}$
$v_{C=N}$: 1631 cm$^{-1}$

EXAMPLE 19

3-[(Pyrrolidin-3-yl)methyl]-6-fluoro-1H-indazole, oxalate

This compound was synthesized using the same process as that described for Example 2 using the compound of Example 18.

Melting point: 165° C.

| Elemental microanalysis: | | | |
|---|---|---|---|
| | C % | H % | N % |
| calculated | 54.37 | 5.21 | 13.59 |
| found | 54.17 | 5.23 | 13.07 |

EXAMPLE 20

3-[(1-Ethoxycarbonylpyrrolidin-3-yl)methyl]-5-cyanoindole

A mixture containing 41 mmol of the compound of Example 14 and 209 mmol of ethyl chloroformate in 400 ml of toluene is brought to reflux for two hours. After evaporation of the solvent, the expected product is obtained by purification of the residue by chromatography on a silica column, using a dichloromethane/methanol/aqueous ammonia (98/2/0.2) mixture as solvent.

Yield: 79%
Infrared spectrum (nujol):
$v_{NH}$: 3255 cm$^{-1}$
$v_{CO}$: 1676 cm$^{-1}$

EXAMPLE 21

3-[(1-Methylpyrrolidin-3-yl)methyl]-5-aminomethylindole

A suspension containing 158 mmol of lithium aluminum hydride in 150 ml of tetrahydrofuran is added at 20° C. to 15.8 mmol of the compound of Example 20 in 50 ml of tetrahydrofuran. The combined mixture is maintained for 9 hours at 20° C. and then hydrolyzed with 30 ml of water and 12 ml of 10% sodium hydroxide solution. After filtration and evaporation, the expected product is obtained in the form of an oil.

Yield: 72%

EXAMPLE 22

3-[(1-Methylpyrrolidin-3-yl)methyl]-5-(methylsulfonaminomethyl) indole 10.6 mmol of triethylamine and then 10.6 mmol of the chloride of methanesulfonic acid are added, at 0° C., to a solution containing 10.6 mmol of the product obtained in the preceding stage in 80 ml of chloroform. The combined mixture is left for two hours at 20° C. and then brought to reflux for 3 hours. After aqueous hydrolysis, extraction with dichloromethane, drying and evaporation, the expected product is obtained after purification by chromatography on a silica column, using a dichloromethane/methanol/aqueous ammonia (80/20/2) mixture as solvent.

Yield: 52%
Infrared spectrum:
$v_{NH}$: 3200 cm$^{-1}$
$v_{SO_2}$: 1311 and 1146 cm$^{-1}$

EXAMPLE 23

1-(4-Fluorophenyl)-3-[(1-ethoxycarbonylpyrrolidin-3-yl)methyl]-5-chloroindole This compound was obtained according to the same process as that described in Example 20 using the compound of Example 11.

Yield: 70%
Infrared spectrum (nujol):
$v_{CO}$: 1676 cm$^{-1}$

EXAMPLE 24

1-(4- Fluorophenyl)-3-[(pyrrolidin-3-yl)methyl]-5-chloroindole, hydrobromide 0.64 mmol of the compound obtained in Example 23 are brought to reflux in 1.4 ml of 48% hydrobromic acid for 1 hour. After cooling, the precipitate is filtered, washed with water and with ether and leads to the expected product.

Yield: 65%
Melting point: 215° C.

| Elemental microanalysis: | | | | |
|---|---|---|---|---|
| | C % | H % | N % | Cl % |
| calculated | 55.70 | 4.67 | 6.84 | 8.65 |
| found | 56.52 | 4.89 | 6.70 | 9.00 |

EXAMPLE 25

3-[(1-Benzylpyrrolidin-3-yl)methyl]-6-fluoro-1,2-benzisoxazole

Stage A:
1-Benzyl-3-[(2,4-difluorophenyl)-2-oxoethyl]-pyrrolidine

This stage is identical to Stage A of Example 18.

Stage B: 1-Benzyl-3-[2-(2,4-difluorophenyl)-2-hydroxy-aminoethyl]pyrrolidine 57 mmol of the compound obtained in the preceding stage, 259 mmol of hydroxylamine hydrochloride, 21.5 ml of triethylamine, 500 ml of anhydrous ethanol and 11.4 ml of a 5N ethanolic hydrochloric acid solution are brought to reflux for 90 minutes. After leaving overnight at 0° C., the triethylamine hydrochloride precipitate is filtered and the filtrate concentrated. After addition of 200 ml of ether, filtration and concentration, the expected product is obtained.

Infrared spectrum (nujol):
$v_{OH}$: between 3500 and 2200 cm$^{-1}$
$v_{C=N/C=C}$: 1614 cm$^{-1}$ Stage C:
3-[(1-Benzylpyrrolidin-3-yl)methyl]-6-fluoro-1,2-benzisoxazole 45 mmol of the compound obtained in the preceding stage are brought to reflux for 2 hours in the presence of 34 g of potassium hydroxide and 42 ml of water. After dilution of the reaction mixture with 300 ml of water, extraction with dichloromethane, drying and evaporation, the expected product is obtained in the form of an oil after purification of the residue by chromatography on a silica column, using a dichloromethane/methanol/aqueous ammonia (98/2/0.2) mixture as eluent.

Infrared spectrum (nujol):
$v_{C=N/C=C}$: 1618 cm$^{-1}$

EXAMPLE 26

3-[(1-Benzylpyrrolidin-3-yl)methyl]-5-aminomethylindole

This compound was synthesized according to the process described in Example 21 from the compound described in Example 14.
Yield: 40%

EXAMPLE 27

3-[(1-Benzylpyrrolidin-3-yl)methyl]-5-methylsulfonamidoindole, hydrochloride

This compound was synthesized according to the process described in Example 22 from the compound described in Example 26.
Melting point: 90° C.

| Elemental microanalysis: | | | | | |
| --- | --- | --- | --- | --- | --- |
|  | C % | H % | N % | Cl % | S % |
| calculated | 60.89 | 6.50 | 9.68 | 8.17 | 7.39 |
| found | 60.61 | 6.74 | 9.49 | 8.09 | 7.73 |

EXAMPLE 28

1-Methyl-3-[(1-benzylpyrrolidin-3-yl)methyl]-5-bromoindole

This compound was synthesized according to the process described in Example 1 from the corresponding starting material.
Yield: 45%

EXAMPLE 29

1-Methyl-3-[(1-benzylpyrrolidin-3-yl)methyl]-5-[2-(aminocarbonyl)vinyl]indole, hydrochloride A mixture containing 2.68 mmol of the compound of Example 28, 3.53 mmol of acrylamide, 0.17 mmol of palladium diacetate, 0.76mmol of tri-ortho-tolyl-phosphine, 0.4ml of triethylamine and 6 ml of aceto-nitrile is heated at 100° C. in a hermetic reactor for 24 hours. The solvent is evaporated and the residue purified by chromatography on a silica column, using a dichloromethane/methanol/aqueous ammonia (95/5/0.5) mixture as eluent. The expected product is then obtained by conversion of the oil to a salt in an ethanolic hydrochloric acid solution and crystallization from ether.

Infrared spectrum (nujol):
$v_{CO}$(amide): 1664 cm$^{-1}$

EXAMPLE 30

1-Methyl-3-[(1-benzylpyrrolidin-3-yl)methyl]-5-[2-(N,N-dimethylaminocarbonyl)-vinyl]indole, hydrochloride The expected product is obtained according to the process described in Example 29, acrylamide being replaced by N,N-dimethylacrylamide.
Melting point: 55° C.

| Elemental microanalysis: | | | | |
| --- | --- | --- | --- | --- |
|  | C % | H % | N % | Cl % |
| calculated | 71.30 | 7.36 | 9.59 | 8.09 |
| found | 71.03 | 7.09 | 9.42 | 8.02 |

EXAMPLE 31

1-Methyl-3-[(1-benzylpyrrolidin-3-yl)methyl]-5-[2-(aminocarbonyl)ethyl]indole, hydrochloride 8.64 mmol of the compound described in Example 29 in 250 ml of ethanol are hydrogenated at room temperature in the presence of 400 mg of 10% palladium-on-charcoal as catalyst. After filtration of the catalyst and evaporation of the solvent, the residue is taken up in ether and the expected product crystallizes.
Melting point: 87° C.
Infrared spectrum (nujol):
$v_{CO}$(amide): 1660 cm$^{-1}$

EXAMPLE 32

1-Methyl-3-[(1-benzylpyrrolidin-3-yl)methyl]-5-[2-(aminosulfonyl)vinyl]indole

The expected product is obtained according to the process described in Example 29, acrylamide being replaced by vinylsulfonamide.
Melting point: 120° C.
Infrared spectrum (nujol):
$v_{SO_2}$: 1331 and 1146 cm$^{-1}$

EXAMPLE 33

1-Methyl-3-[(1-benzylpyrrolidin-3-yl)methyl]-5-[2-(aminosulfonyl)ethyl]indole, hydrochloride The expected product is obtained according to the process described in Example 31 from the compound described in Example 32.
Melting point: 88° C.

| Elemental microanalysis: | | | | |
|---|---|---|---|---|
| | C % | H % | N % | Cl % |
| calculated | 61.66 | 6.75 | 9.38 | 7.91 |
| found | 61.54 | 6.88 | 9.52 | 7.76 |

EXAMPLE 34

1-Methyl-3-[(1-benzylpyrrolidin-3-yl)methyl]-5-cyanoindole

The expected product is obtained according to the process described in Example 14 using the compound of Example 28.
Infrared spectrum (liquid film):
$\nu_{C\equiv N}$: 2218 cm$^{-1}$

EXAMPLE 35

1-Methyl-3-[(1-benzylpyrrolidin-3-yl)methyl]-5-aminomethylindole

The expected product is obtained according to the process described in Example 21 using the compound of Example 34.
Infrared spectrum (nujol):
$\nu_{C=C}$(aromatic): 1603 cm$^{-1}$

EXAMPLE 36

1-Methyl-3-[(1-benzylpyrrolidin-3-yl)methyl]-5-(methylsulfonylaminomethyl)indole, hydrochloride The expected product is obtained according to the process described in Example 22 using the compound of Example 35.
Melting point: 140° C.

| Elemental microanalysis: | | | | | |
|---|---|---|---|---|---|
| | C % | H % | N % | S % | Cl % |
| calculated | 61.66 | 6.75 | 9.38 | 7.16 | 7.91 |
| found | 61.63 | 6.86 | 9.39 | 7.16 | 8.01 |

EXAMPLE 37

1-Methyl-3-[(1-ethoxycarbonylpyrrolidin-3-yl)methyl]-5-cyanoindole

The expected product is obtained according to the process described in Example 20 using the compound of Example 34.
Infrared spectrum (nujol):
$\nu_{C\equiv N}$: 2218 cm$^{-1}$
$\nu_{CO}$: 1697 cm$^{-1}$

EXAMPLE 38

1-Methyl-3-[(1-methylpyrrolidin-3-yl)methyl]-5-aminomethylindole

The expected product is obtained according to the process described in Example 21 using the compound of Example 37.

EXAMPLE 39

1-Methyl-3-[(1-methylpyrrolidin-3-yl)methyl]-5-(methylsulfonylaminomethyl)indole, hydrochloride The expected product is obtained according to the process described in Example 22 using the compound of Example 38.
Melting point: 84° C.

EXAMPLE 40

1-Methyl-3-[(1-benzylpyrrolidin-3-yl)methyl]-5-[(2-oxoimidazolidino)methyl]indole, hydrochloride 5.55 mmol of β-chloroethyl isocyanate are added, at −5° C., to a solution containing 5.55 mmol of the compound of Example 35 in 100 ml of anhydrous chloroform. After evaporation of the solvent at room temperature, the residue is taken up in 100 ml of tetrahydrofuran. 13 ml of butyllithium as a 15% solution in hexane are added dropwise at −5° C. to the above mixture. After reacting for one hour at 0° C., the mixture is hydrolyzed with a saturated ammonium chloride solution. After separation by settling, extraction with dichloromethane, drying and evaporation, the expected product is obtained and is purified by chromatography on a silica column, using a dichloromethane/methanol/aqueous ammonia (95/5/0.5) mixture as eluent. The hydrochloride is obtained by treatment in ethanolic hydrochloric acid.
Melting point: 130° C.

EXAMPLE 41

3-[(1-Ethoxycarbonylpyrrolidin-3-yl)methyl]-5-bromoindole

The expected product is obtained by using the process described in Example 20 using the compound of Example 12.

EXAMPLE 42

3-[(1-Methylpyrrolidin-3-yl)methyl]-5-bromoindole

The expected product is obtained according to the process described in Example 21 using the compound of Example 41.

EXAMPLE 43

3-[(1-Methylpyrrolidin-3-yl)methyl]-5-[2-(methylaminosulfonyl)vinyl]indole

The expected product is obtained according to the process described in Example 29 using the compound of Example 42 and replacing acrylamide with N-methylvinyl-sulfonamide (prepared according to the process described in U.S. Pat. No. 3,761,473).

EXAMPLE 44

3-[(1-Methylpyrrolidin-3-yl)methyl]-5-[2-(methylaminosulfonyl)ethyl]indole, hydrochloride The expected product is obtained according to the process described in Example 31 using the compound of Example 43.
Mass spectrum: NH$_3$ Ionization:
M+H$^+$: m/z=336 (theoretical M: 335)

EXAMPLE 45

3-[(1-Benzylpyrrolidin-3-yl)methyl]-5-[5-methyl-1,2,4-oxadiazol-3-yl]indole

A solution containing 12.7 mmol of sodium methoxide in 5 ml of methanol is added to a solution containing 12.7 mmol of hydroxylamine hydrochloride in 15 ml of methanol. The mixture is stirred for one hour at room temperature. After filtration of the precipitate, 5.7 mmol of the compound of Example 14 are added to the filtrate and the combined mixture is brought to reflux for 48 hours. After evaporation of the solvent, the brown solid obtained is mixed with 10 ml of acetic anhydride. The combined mixture is heated for 24 hours at 80° C. After hydrolysis with water, the combined mixture is brought to pH=12 using 2N sodium hydroxide solution. After extraction with dichloromethane, drying and evaporation, the expected product is obtained after purification of the residue by chromatography on a silica column, using a dichloromethane/methanol/aqueous ammonia (95/5/0.5) mixture as eluent.

EXAMPLE 46

3-[(1-Benzylpyrrolidin-3-yl)methyl]-5-[1,2,3,5-oxa-thiadiazol-2-oxo-4-yl]indole The expected product is obtained according to the process described in Example 45, acetic anhydride being replaced by thionyl chloride.

EXAMPLE 47

3-[(1-Benzylpyrrolidin-3-yl)methyl]-5-[3-methyl-1,2,4-oxadiazol-5-yl]indole

PHARMACOLOGICAL STUDY OF THE COMPOUNDS OF THE INVENTION

EXAMPLE 48

Contraction of the vena saphena

Experiments are carried out on venae saphenae of dogs (10–25kg) or rabbits (2–3 kg) anesthetized with pentobarbital (30 mg/kg i.v.). The venae saphenae are rapidly removed and cut into rings. These rings are mounted between two hooks in tanks thermostatically controlled at 37° C. containing physiological solution (composition in mM: NaCl118.3; KCl 4.7; CaCl$_2$2.5; MgSO$_4$1.2; KH$_2$PO$_4$1.2; NaHCO$_3$25.0; Ca-EDTA 0.026 and glucose 11.1). A mixture of 95% O$_2$/5% CO$_2$ is bubbled through the physiological solution. The lower hook constitutes the fixed point whereas the upper hook is connected to an isometric force sensor. The tissues are put under a base tension of 1.5 grams (dogs) and 1 gram (rabbits). The pharmacological substances studied are prepared immediately before use; they are dissolved in water or in dimethyl sulfoxide.

After mounting, the preparations are left standing for 60 minutes, rinsings being carried out every 30 minutes. The organ is then brought into contact with phenoxybenzamine ($5 \times 10^{-8}$ M) for 20 minutes. This agent is removed by several successive washings over 45 minutes. After readjusting the base tension, a contraction is caused by KCl (100 mM). After washing and returning to the base line, a contraction is induced by 5-hydroxytryptamine ($10^{-5}$ M).

After washing and returning to the base line, a dose/-response curve with the pharmacological substances is produced by addition of cumulative doses ($10^{-9}$ to $10^{-4}$ M).

This experiment makes it possible to calculate the 50% effective concentration (EC$_{50}$) of the compounds of the invention.

This EC$_{50}$ is calculated in the following way: the tension values are first converted to percentages with respect to the maximum effect induced by KCl. The 50% effective concentration (EC$_{50}$) is determined by nonlinear regression according to the model of the Michaelis-Menten mass action law.

The specificity for the 5-HT$_1$ receptor of the vein is confirmed by using specific antagonists such as metitepine (5-HT$_1$/5-HT$_2$ antagonist) and ketanserin (5-HT$_2$ antagonist). In this test, the EC$_{50}$ determined on the vena saphena of dogs for the compound of Example 17 is equal to 0.34 μM whereas that of sumatriptan is equal to 0.64 μM.

The EC$_{50}$ on the vena saphena of rabbits of the compound of Example 17 is equal to 0.41 μM.

PHARMACEUTICAL COMPOSITION

EXAMPLE 49

Pharmaceutical composition

| Formula for the preparation of 1000 tablets containing a dose of 10 mg: | |
|---|---|
| Compound of Example 17 | 10 g |
| Hydroxypropyl cellulose | 2 g |
| Wheat starch | 10 g |
| Lactose | 100 g |
| Magnesium stearate | 3 g |
| Talc | 3 g |

We claim:

1. A compound of formula (I):

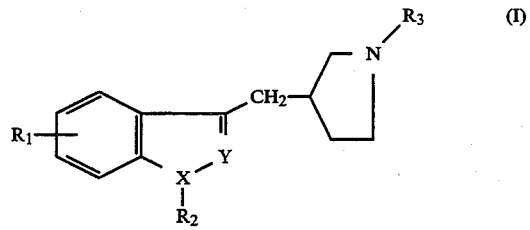

in which:

R$_1$ represents hydrogen, halogen, linear or branched (C$_1$–C$_6$)alkyl, linear or branched (C$_1$–C$_6$)-alkoxy, cyano, or aminocarbonyl, or any one of the following groups:

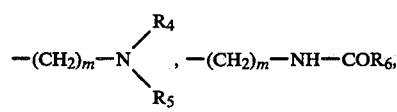

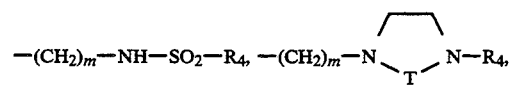

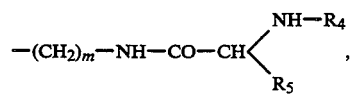

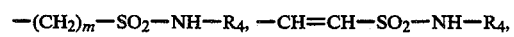

-continued

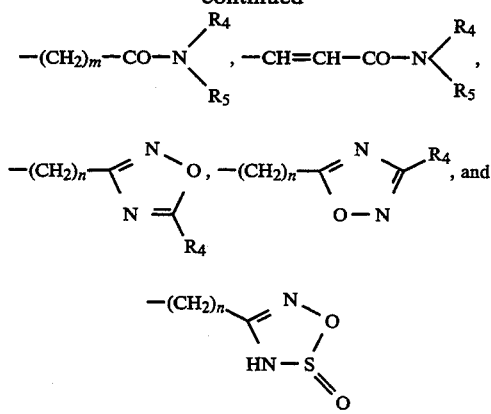

in which
m is equal to 1, 2 or 3,
n is equal to 0, 1 or 2,
T represents CO or SO₂,
R₄ or R₅, which are identical or different, represent hydrogen, linear or branched (C₁-C₆)alkyl, or phenyl (unsubstituted or substituted by one or a number of halogen, alkyl, alkoxy, or trihalomethyl),
R₂ represents hydrogen, linear or branched (C₁-C₆)alkyl, phenyl (unsubstituted or substituted by one or a number of halogen, alkyl, alkoxy, or trihalomethyl) or acyl,
R₃ represents hydrogen, linear or branched (C₁-C₆)alkyl (optionally substituted by hydroxyl or phenyl (itself unsubstituted or substituted by one or a number of halogen, alkyl, alkoxy, or trihalomethyl)), or linear or branched (C₁-C₆)alkoxycarbonyl, —X—Y= represents —N—C=, —N—N= or else

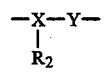

represents —O—N=;
its enantiomers, diastereoisomers and epimers, and its addition salts with a pharmaceutically-acceptable acid.

2. A compound of claim 1, in which —X—Y= represents —N—C=, its enantiomers, diastereoisomers and epimers, and its addition salts with a pharmaceutically-acceptable acid.

3. A compound of claim 1, in which —X—Y= represents —N—N=, its enantiomers, diastereoisomers and epimers, and its addition salts with a pharmaceutically-acceptable acid.

4. A compound of claim 1, in which

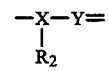

represents —O—N=,
its enantiomers, diastereoisomers and epimers, and its addition salts with a pharmaceutically-acceptable acid.

5. A compound of claim 1, in which R₂ represents hydrogen, its enantiomers, diastereoisomers and epimers, and its addition salts with a pharmaceutically-acceptable acid.

6. A compound of claim 1, in which R₁ is located in the 5-position of the phenyl ring, its enantiomers, diastereoisomers and epimers, and its addition salts with a pharmaceutically-acceptable acid.

7. A compound of claim 1, in which R₃ represents benzyl, its enantiomers, diastereoisomers and epimers, and its addition salts with a pharmaceutically-acceptable acid.

8. A compound of claim 1, in which R₃ represents linear or branched (C₁-C₆)alkyl, its enantiomers, diastereoisomers and epimers, and its addition salts with a pharmaceutically-acceptable acid.

9. A compound of claim 1 which is 3-[(1-propylpyrrolidin-3-yl)methyl]-5-amino-carbonylindole, its enantiomers, and its addition salts with a pharmaceutically-acceptable acid.

10. A method for treating an animal living body afflicted with migraine comprising the step of administering to the living body an amount of a compound of claim 1 which is effective for alleviation of said condition.

11. A pharmaceutical composition useful in treating migraine comprising as active principle an effective amount of a compound of claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,348,968

DATED : September 20, 1994

INVENTOR(S) : Gilbert Lavielle, Philippe Maillos, Olivier Muller, Michel Laubie
Tony Verbeuren, Jean-Jacques Descombes It is certified that error appears in the above-indentified patent and that said Letters Patent is hereby corrected as shown below:

Column 4, line 5; "BrB'$_3$" should read -- BrR'$_3$ --
Column 6, line 15; "BrB'$_3$" should read -- BrR'$_3$ --
Column 7, line 28; the formula, "R$_3$" and "(I$_2$)" are on top of each other so you can't read them.
Print "R$_3$" and "(I$_2$)" so you can read them, and separate 3 spaces.
Column 7, line 55; the formula, "R$_3$" and "(I$_3$)" are on top of each other so you can't read them.
Print "R$_3$" and "(I$_3$)" so you can read them, and separate 3 spaces.
Column 8, line 15; the formula, "R$_3$" and "(I$_4$)" are on top of each other so you can't read them.
Print "R$_3$" and "(I$_4$)" so you can read them, and separate 3 spaces.
Column 10, line 49; "Missing" should read -- Melting --
Column 22, line 42; insert a comma after the word "migraine"

Signed and Sealed this

Twentieth Day of December, 1994

Attest:

BRUCE LEHMAN

*Attesting Officer*  *Commissioner of Patents and Trademarks*